United States Patent [19]

Andersen

[11] Patent Number: 4,715,710
[45] Date of Patent: Dec. 29, 1987

[54] PUMP COLORIMETRIC ANALYZER

[75] Inventor: Marinus L. Andersen, Loveland, Colo.

[73] Assignee: Hach Company, Loveland, Colo.

[21] Appl. No.: 830,969

[22] Filed: Feb. 19, 1986

[51] Int. Cl.⁴ .................. G01N 1/10; G01N 21/85
[52] U.S. Cl. .................. 356/246; 356/244; 356/410
[58] Field of Search .................. 356/246, 410, 244

[56] References Cited

U.S. PATENT DOCUMENTS

| | | | |
|---|---|---|---|
| 3,118,390 | 1/1964 | Kingsley | 103/227 |
| 3,418,061 | 12/1968 | Schultz | 356/246 |
| 3,607,082 | 9/1971 | Thiers | 23/230 |
| 3,607,095 | 9/1971 | Etzlinger | 23/254 R |
| 3,932,065 | 1/1976 | Ginsberg et al. | 417/317 |
| 4,053,282 | 10/1977 | Hach et al. | 23/230 R |
| 4,288,308 | 9/1981 | Hach | 204/195 R |
| 4,291,986 | 9/1981 | Satou et al. | 356/410 |

Primary Examiner—Vincent P. McGraw
Assistant Examiner—S. A. Turner
Attorney, Agent, or Firm—Dean P. Edmundson

[57] ABSTRACT

A pump colorimetric analyzer is described including: (a) a sample cell through which a light beam is transmitted, (b) a light source, (c) a photodetector, and (d) a piston which reciprocates between first and second positions in the cell. The piston includes a sample chamber which permits the light beam to be transmitted therethrough when the piston is in its second position. When the piston is in its first position the light beam is transmitted through the sample cell. The novel analyzer uses a single light source, a single sample cell and a single photodetector.

20 Claims, 5 Drawing Figures

PUMP COLORIMETRIC ANALYZER

FIELD OF THE INVENTION

This invention relates to the field of colorimetric chemical analysis. More particularly, it relates to improved apparatus and techniques for reliably comparing light transmittance through a prepared liquid sample with light transmittance through a control sample.

BACKGROUND OF THE INVENTION

The technique of colorimetric chemical analysis of liquids is well established. The classic method involves transmitting a light beam transversely through a transparent cell (for example, a glass cylinder) containing a liquid sample to be tested. To the liquid sample (such as water containing a foreign substance whose concentration is to be measured) are added appropriate types and amounts of reagents which will react with the foreign substance in the sample and form a color. The degree of transmittance of the light beam through the cell containing the liquid sample will be directly affected by the degree of color formation in the liquid sample (resulting from the concentration of the foreign substance in the liquid sample). The degree of light transmittance through the liquid sample, as measured by a photodetector, is compared with other samples containing known concentrations of the same foreign substance in order to determine the quantitative amount of the foreign substance in the tested sample. When using this classic technique a control sample of liquid (which does not contain any of the color forming reagents) in a separate cell is used in the colorimeter as a baseline for light transmittance.

One of the main disadvantages of the classic technique is that separate sample cells are used for the sample to be tested, the control sample (i.e., without reagents), and the samples of known concentrations of the foreign substance. Because of the variance in the amount of light absorbance by the walls of the different sample cells, there are inherent inaccuracies in the results obtained from the testing.

As is known in the art, the concentration of the foreign substance in the liquid sample is related to the photocell current developed by the photocell, the concentration being proportional to log (I ref./I sig.), where I ref. is the photocell current when no color-forming reagent is in the sample and I sig. is the photocell current after the color in the sample has been developed.

The simplest type of analyzer would have one sample cell, one light beam, and one photodetector. The instrument would require periodic standardization by introducing a pure liquid sample (i.e., a liquid sample not containing the foreign substance being tested for) which contains no color-producing means, and then making appropriate adjustments so as to make current A (the photocell output) equal to current B (a fixed current) such that the log amp output is zero. Span adjustment is achieved by introducing a standard solution of known concentration of foreign substance and adjusting the log amp gain until the instrument reads the proper value. The instrument would now read the proper value. Such an instrument has no provision for automatically compensating for drifts due to sample aging, temperature, or dirty optical windows; hence, it is suitable only for less exacting analysis.

Some of the disadvantages associated with use of the classic technique have been alleviated by means of a technique involving a single simple cell and a beam splitter which directs a portion of the light beam through a filter to a reference detector and the main part of the light beam through a second filter to a sample detector. The wavelengths of light passed by the two filters are predetermined based upon the particular sample parameter being tested. However, this technique also has associated disadvantages. For example, it requires that two photodetectors be used. The two photodetectors may drift or vary with temperature at different rates, particularly since they are measuring different wavelengths of light. Also, if there is turbidity in the sample it could absorb light differently at the different wavelengths. Another disadvantage is that it may not be possible to find a reference wavelength which is not absorbed to some extent by the color in the sample cell.

Another known technique involves an analyzer in which a single light source is used in conjunction with two sample cells, two color filters of the same type, and two photodetectors. The liquid sample is first introduced into sample cell B without any color-forming reagents present. The light transmitted through the sample reaches photodetector B (where current B is generated). The liquid sample is then transferred to sample cell A (with color forming reagents added enroute). The light transmitted through the prepared sample reaches photodetector A (where current A is generated). Such an analyzer is not affected by lamp aging or temperature-related drifts in the sample but it does have the disadvantage of having two sets of optical surfaces which may become dirty at different rates. Also, the two photodetectors may have different temperature drift characteristics.

Yet another technique involves a dual beam photometer. A light beam from a single light source is divided into two separate beams, one of the beams being directed through a sample cell containing the reference standard and the other beam being directed through a separate sample cell containing the sample to be tested. The same photodetector is used to measure light transmittance through both the reference cell and the sample cell. There are inherent limitations associated with this technique, however. For example, the sample cell and the reference cell may be of slightly different sizes. Also, the surface conditions of the reference cell and sample cell may be different. These types of differences, of course, may have a significant effect on the accuracy of the technique.

SUMMARY OF THE INVENTION

In accordance with the present invention there is provided an improved pump colorimetric analyzer which comprises:

(a) a sample cell adapted to permit a light beam to be transmitted therethrough;

(b) a light source adapted to transmit a light beam through said sample cell;

(c) a photodetector adapted to detect light transmittance through said sample cell from said light source;

(d) a piston adapted to reciprocate between first and second positions within said sample cell, said piston having a sample chamber therein which is adapted to permit said light beam from said light source to be transmitted through said chamber in said piston to said photodetector when said piston is in said second position, said piston further including means for introducing a liquid sample into said chamber and expelling said liquid sample from said chamber.

The analyzer is adapted to measure light transmittance through a first liquid sample (e.g., the liquid without color-forming agents therein) present in the sample chamber when the piston is in the second position and is adapted to measure light transmittance through a second liquid sample (e.g., the same liquid with color-forming agents added) present in the sample cell when the piston is in the first position.

In the analyzer of this invention, the light source, optical surfaces, color filter, length of the light paths, and photodetector are the same when measuring light transmittance through the reference liquid and the sample being tested, thus avoiding common disadvantages associated with previous analyzers.

BRIEF DESCRIPTION OF THE DRAWINGS

The apparatus of the invention is illustrated in the accompanying drawings wherein like reference characters refer to the same parts throughout the several views and in which.

DETAILED DESCRIPTION OF THE INVENTION

Figure 1:
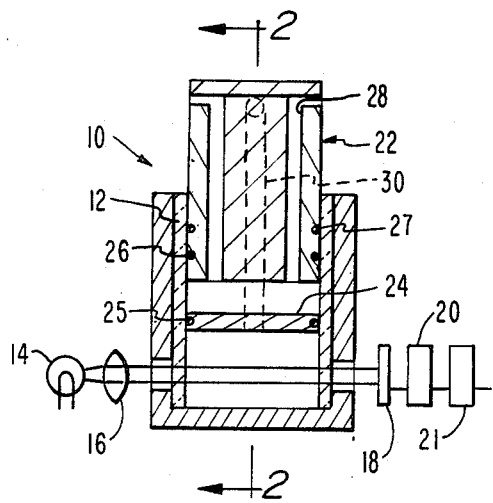
FIG. 1 is an elevational view, in cross-section, of the apparatus of the invention with the piston in its first position.

In the drawings there is shown a pump colorimetric analyzer 10 comprising a sample cell 12 which is adapted to permit a light beam from light source 14 to be transmitted therethrough. Lens 16 is present to collimate the light from source 14. After passing through sample cell 12 the light beam passes through conventional color filter 18 and is received by a conventional photodetector 20. In a preferred embodiment the sample cell 12 comprises a glass cylinder, although it may be composed of any fluid impervious material (e.g., metal or plastic) so long as it is transparent to the light beam from light source 14 along some portion of its length.

Figure 2:
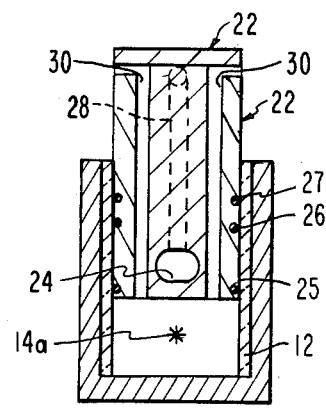
FIG. 2 is a side elevational view, in a cross-section, along line 2—2 of the apparatus shown in FIG. 1.
Figure 3:
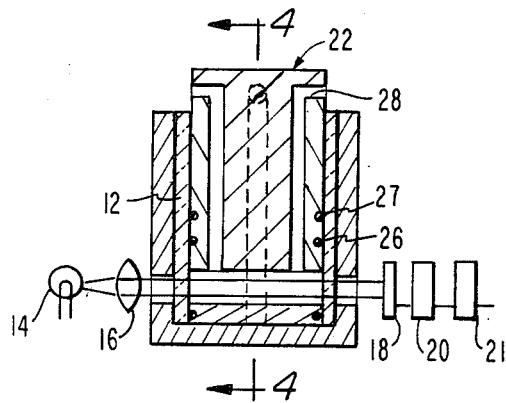
FIG. 3 is an elevational view, in cross-section, of the apparatus of the invention with the piston in its second position.
Figure 4:
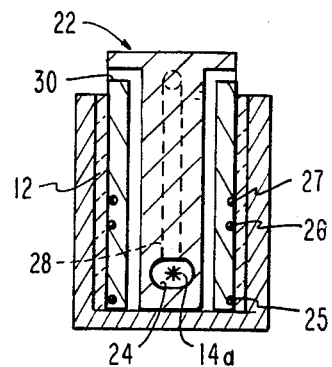
FIG. 4 is a side elevational view, in a cross-section, along line 4—4 of the apparatus shown in FIG. 3.

Piston 22 is fitted within cell 12 and is adapted to reciprocate between a first position (for example, an outward position) as shown in FIGS. 1 and 2 and a second position (for example, an inward position) as shown in FIGS. 3 and 4. Piston 22 includes a sample chamber 24 which is adapted to permit the light beam from light source 14 to be transmitted through chamber 24 to photodetector 20 when piston 22 is in the second position (as shown in FIGS. 3 and 4). Chamber 24, in a preferred embodiment, comprises an opening which extends transversely through piston 22. Chamber 24 is isolated by means of seals 25 and 26 which may be, for example, O-rings, so that liquid contained in chamber 24 cannot leak out into cell 12. It is preferred to include an additional seal system 27 which may be, for example, an O-ring behind a cup seal. A water wash between seals 26 and 27 is very desirable because it prevents air from leaking past seal 26 when piston 22 moves outwardly and it also prevents any color-forming reagents which may have leaked outward past seal 26 from depositing in the area between seals 26 and 27. In one embodiment the inlet sample stream is passed through the area between seals 26 and 27 so as to continually flush this area of material to prevent deposits or films from forming there.

Piston 22 further includes means for introducing a liquid sample into chamber 24 and expelling the sample at the conclusion of the testing. In a preferred embodiment passageway or conduit 28 in piston 22 communicates between a source of liquid sample and chamber 24, as shown in FIGS. 1 and 3.

Piston 22 also includes means for introducing a liquid sample into sample cell 12. In a preferred embodiment passageway 30 through piston 22 communicates between a source of liquid sample and cell 12, as shown in FIGS. 2 and 4. When piston 22 moves from its first (outward) position to its second (inward) position, piston 22 displaces the liquid sample contained in sample cell 12 by forcing the liquid through passageway 30.

In one embodiment, the liquid sample (without the presence of color-forming reagents) is introduced into chamber 24 in piston 22. With the piston in its inward position the light beam 14a is transmitted through the sample in the chamber 24 and is received by the photodetector 20. The output from the photodetector 20 is received by an analog-to-digital converter 21 which converts the light transmittance or absorbance data to a digital signal. Then the digitized information proceeds to a conventional microprocessor.

Then piston 22 moves outward to its second position. To the sample which was previously present in the chamber 24 are added the requisite types and amounts of color-forming reagents, after which the sample may be permitted to age for a predetermined period of time, if required, in order to develop the color. The sample is then introduced into sample cell 12 via passageway 30, whereupon the light beam from light source 14 is shone through the sample and received by photodetector 20. The signal received from the photodetector 20 is then digitized by converter 21.

In this manner the same liquid sample is tested in the same cell, with the same light source and photodetector, before and after the color-forming reagents are added. Thus, all of the parameters in the system remain constant except for the addition of color-forming reagents to the liquid sample. Consequently, much more accurate and reliable test results are obtained than when using prior art techniques.

Figure 5:
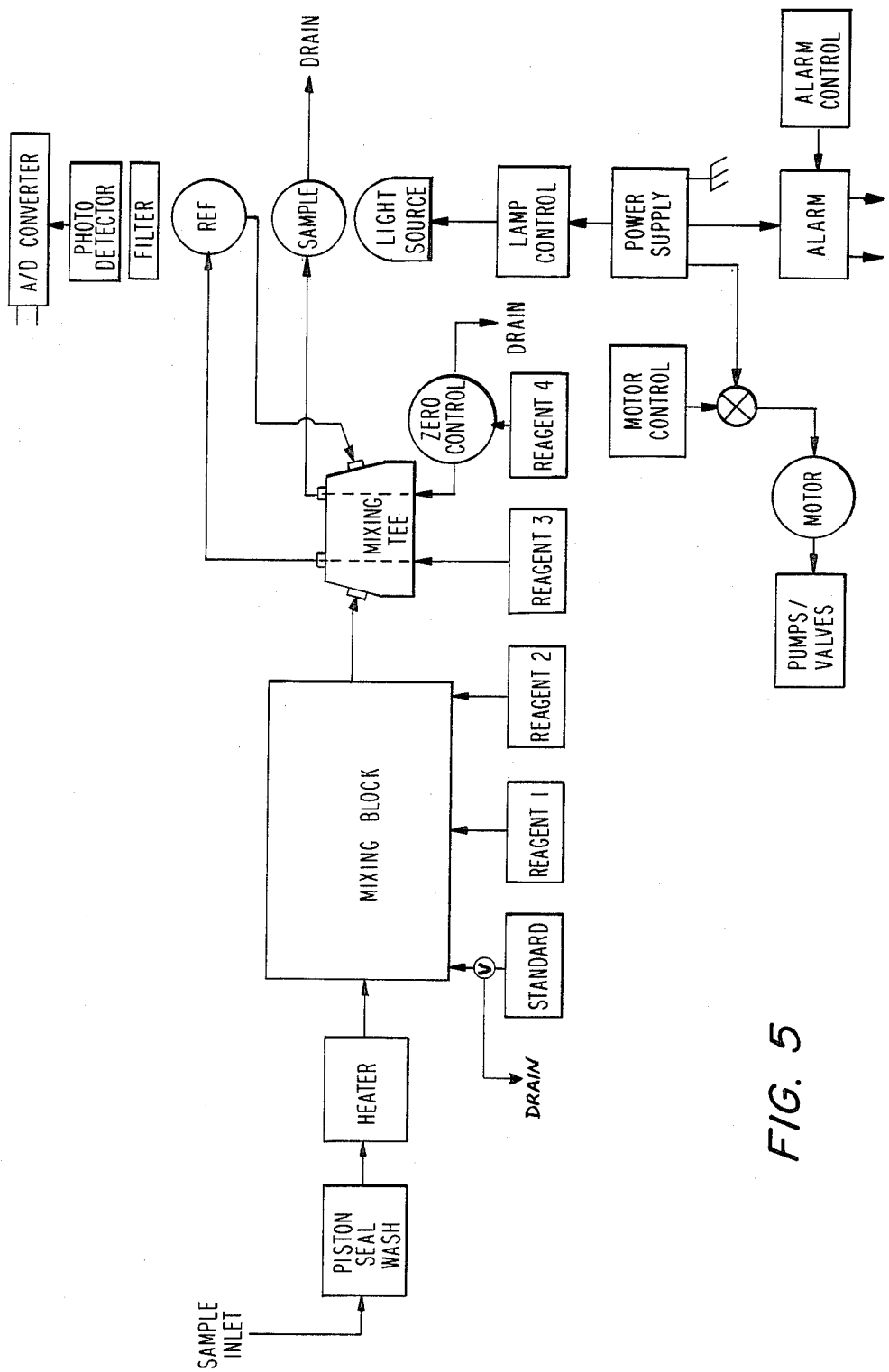
FIG. 5 is a schematic drawing showing the manner in which the liquid sample to be tested proceeds through various stages in one embodiment of the invention.

In FIG. 5 there is shown, schematically, the manner in which a liquid sample is processed in one embodiment of the invention. Thus, a liquid sample is first drawn or collected (e.g., a water sample taken from the inlet pipe leading to a boiler). In one embodiment the liquid sample is passed through the area between the seals 26 and 27 surrounding piston 22 to flush it out and prevent the formation of a film or deposit therein.

Depending upon the type of test to be run, the sample may then be heated to a predetermined temperature. The necessary amount of liquid sample required for testing (e.g., 5 ml.) is retained and any excess is discarded to a drain.

To this liquid sample there are added appropriate amounts of non-color-forming reagents. For example, when testing a water sample for concentration of silica therein, a surfactant and a molybdate salt may be added to the sample in a mixing block. These ingredients will not cause a color formation, by themselves, in the water. Then the sample proceeds to a mixing tee where citric acid is added to the sample, after which the sample proceeds to the chamber 24 in the piston 22 where light is transmitted through the sample. The transmitted light is received by the photodetector and the light absorbance data is digitized by the converter 21.

The sample is then removed from the chamber 24 in the piston 22 of the novel apparatus and returned to the mixing tee where an amino acid compound is added to the sample. The sample then develops a color whose intensity is dependent upon the amount of silica present therein. The sample is then introduced into the sample cell 12 where light from the single light source 14 is transmitted through the sample and received by the photodetector. The signal generated by the photodetector is digitized and represents the sample signal which is then compared to the signal generated by the photodetector when the non-colored precursor sample was tested. The sample is then discarded to a drain.

In the process illustrated in the schematic of FIG. 5, the "standard" is a sample with a known concentration of the foreign substance being detected (e.g., silica). Periodically a sample of this "standard" is passed through valve V to the mixing block and then processed through the analyzer to assure that the analyzer is properly calibrated. The standard correction is determined by running the sample of known concentration through the apparatus and obtaining a light transmittance value which then may be used as a standard. A conventional microprocessor may be used to compare the values of the light transmittance through the reference sample and the final colored sample and correct it, if necessary, in accordance with the light transmittance through the standard sample of known concentration.

The "Zero Control" refers to a conventional technique in which a sample of the liquid being tested is periodically processed without adding the color-forming reagents. A microprocessor adjusts a correction factor to produce a zero value.

In a preferred situation the analyzer of the invention is used to continuously monitor a feed stream for determination of the concentration of any desired foreign substance. The results of such monitoring may be displayed in known fashion on a chart recorder or direct reading dial, gauge, monitor, or light indicator. If desired, it is also possible to interconnect an alarm system to the display or read-out indicator for the purpose of sounding an alarm in the event that the concentration of the foreign substance wanders beyond prescribed limits.

Of course, it is not necessary to use the analyzer of the invention as a continuous monitoring mode. Batch testing of prepared liquid samples may also be conducted, at the desire of the operator.

Other variants are possible without departing from the scope of this invention.

What is claimed is:

1. A pump colorimetric analyzer comprising:
    (a) a sample cell adapted to permit a light beam to be transmitted therethrough;
    (b) a light source adapted to transmit a light beam through said sample cell;
    (c) a photodetector adapted to detect light transmittance through said sample cell from said light source;
    (d) a piston adapted to reciprocate between first and second positions within said sample cell, said piston having a sample chamber therein which is adapted to permit said light beam from said light source to be transmitted through said chamber in said piston to said photodetector when said piston is in said second position, said piston further including means for introducing a liquid sample into said chamber and expelling said liquid sample from said chamber;

wherein said analyzer is adapted to measure light transmittance through a first liquid sample present in said sample cell when said piston is in said first position and is adapted to measure light transmittance through a second liquid sample present in said sample chamber when said piston is in said second position.

2. A pump colorimetric analyzer in accordance with claim 1, wherein said sample cell comprises a glass cylinder.

3. A pump colorimetric analyzer in accordance with claim 1, wherein said chamber in said piston comprises an opening extending transversely through said piston.

4. A pump colorimetric analyzer in accordance with claim 1, wherein said piston includes at least one passageway which communicates between said sample cell and a source of liquid sample.

5. A pump colorimetric analyzer in accordance with claim 1, wherein said piston includes at least one passageway which communicates between said chamber and a source of liquid sample.

6. A pump colorimetric analyzer in accordance with claim 1, wherein said piston is adapted to displace a liquid sample from said sample cell when said piston moves from said first position to said second position.

7. A pump colorimetric analyzer in accordance with claim 1, further comprising means for transmitting a liquid sample from said sample chamber to said sample cell.

8. A pump colorimetric analyzer in accordance with claim 7, further comprising means for adding color-forming reagents to said liquid sample before it is introduced into said sample cell.

9. A pump colorimetric analyzer in accordance with claim 3, wherein the periphery of said piston includes at least two seals, the first said seal being disposed below said chamber and the second seal being disposed above said chamber.

10. A pump colorimetric analyzer in accordance with claim 9, wherein each of said seals comprises a cup seal in combination with an O-ring.

11. A pump colorimetric analyzer in accordance with claim 9, wherein the periphery of said piston includes a third seal disposed above said second seal.

12. A pump colorimetric analyzer in accordance with claim 1, further comprising means for transmitting a liquid sample from said sample chamber to said sample cell.

13. A pump colorimetric analyzer comprising:
    (a) a sample cell adapted to permit a light beam to be transmitted therethrough;
    (b) a light source adapted to transmit a light beam through said sample cell;
    (c) a photodetector adapted to detect light transmittance through said sample from said light source;
    (d) a piston adapted to reciprocate between first and second positions within said sample cell, said piston having a sample chamber therein which is adapted to permit said light beam from said light source to be transmitted through said chamber in said piston to said photodetector when said piston is in said second position, said piston further including conduit means for introducing a second liquid sample into said chamber and for expelling said second liquid sample from said chamber, said piston further including passageway means for introducing a first liquid sample into said cell and for expelling said first sample from said cell;
wherein said analyzer is adapted to measure light transmittance through said first liquid sample present in said sample cell when said piston is in said first position and is adapted to measure light transmittance through said second liquid sample present in said sample chamber when said piston is in said second position.

14. A pump colorimetric analyzer in accordance with claim 13, wherein said cell comprises a glass cylinder.

15. A pump colorimetric analyzer in accordance with claim 13, wherein said chamber in said piston comprises an opening extending transversely through said piston.

16. A pump colorimetric analyzer in accordance with claim 13, wherein said piston is adapted to displace said first liquid sample from said sample cell when said piston moves from said first position to said second position.

17. A pump colorimetric analyzer in accordance with claim 13, further comprising means for transmitting said first liquid sample from said sample chamber to said sample cell.

18. A pump colorimetric analyzer in accordance with claim 17, further comprising means for adding color-forming reagents to said first liquid sample before it is introduced into said sample cell.

19. A pump colorimetric analyzer in accordance with claim 13, wherein the periphery of said piston includes at least two seals, the first said seal being disposed below said chamber and the second said seal being disposed above said chamber.

20. A pump colorimetric analyzer in accordance with claim 19, wherein said periphery of said piston includes a third seal disposed above said second seal.

* * * * *